United States Patent [19]

Nohira et al.

[11] Patent Number: 4,621,151

[45] Date of Patent: Nov. 4, 1986

[54] OPTICAL RESOLUTION OF DL-CYSTEINE

[75] Inventors: Hiroyuki Nohira, 51-5 Ohkubo Ryoke, Urawa Saitama-ken; Keiko Ueda, Chiba, both of Japan

[73] Assignee: Hiroyuki Nohira, Urawa, Japan

[21] Appl. No.: 375,686

[22] Filed: May 6, 1982

[30] Foreign Application Priority Data

May 21, 1981 [JP] Japan ................................. 56-75686

[51] Int. Cl.$^4$ ............................................. C07B 57/00
[52] U.S. Cl. ............................. 562/401; 260/501.12; 562/402; 562/557
[58] Field of Search ................................. 562/401, 402

[56] References Cited

U.S. PATENT DOCUMENTS 4,198,524  4/1980  Tashiro et al. ....................... 562/401

FOREIGN PATENT DOCUMENTS 51-29293  9/1976  Japan .
53-119844  3/1977  Japan .

OTHER PUBLICATIONS

J. Chem. Soc. Jpn. 92 (11) 999 (1971).

Primary Examiner—Natalie Trousof
Assistant Examiner—Vera C. Clarke
Attorney, Agent, or Firm—Armstrong, Nikaido, Marmelstein & Kubovcik

[57] ABSTRACT

Disclosed is a method of optical resolution of DL-cysteine utilizing optically active mandelic acid. The method facilitates commercial production of optically active cysteine, particularly L-cysteine which is in great demand.

1 Claim, No Drawings

OPTICAL RESOLUTION OF DL-CYSTEINE

BACKGROUND OF THE INVENTION

1. Filed of the Invention

The present invention concerns optical resolution of DL-cysteine, or, in other words, a method of producing optically active cysteine or cystine.

2. State of the Art

L-cysteine is produced nowadays mainly by extracting it from natural raw materials. Because this way of production cannot meet rapidly increasing demand, other ways of industrial production such as chemical synthesis or fermentation methods have been sought. In cases according to the synthesis, the product will be in DL-form, and therefore, it should be optically resolved to obtain L-cysteine.

General methods of optically resolving DL-amino acids known to date are preferential crystallization, resolution with enzymes, and diastereomer resolution. As far as DL-cysteine is concerned, because it is chemically rather unstable and racemization reaction is difficult to occur, there has been established no method of commercially practicable optical resolution by the preferential crystalization or diastereomer resolution.

With respect to the method of resolution using the enzyme, Japanese Patent Disclosure No. 29293/1976 describes a method of effecting acylase to S-alkyl- or aryl-mercapto-N-acyl-DL-cysteine to obtain optically active S-alkyl- or aryl-mercapto-cysteine, and reducing the latter to form optically active cysteine. The method cannot be said advantageous for commercial practice, because the method not only uses the enzyme which is an organism substance, but also requires multiple steps of N-acylation, S-alkyl- or aryl-mercaptization, and further, dealkyl- or dearyl-mercaptization.

On the other hand, as an example of optically resolving certain DL-amino acids with optically active resolving agent, a method using mandelic acid was disclosed in Japanese Patent Disclosure No. 119844/1978. Also, use of L-phenyl alanine for optical resolution of mandelic acid was reported in J. Chem. Soc. Jpn. 92 (11) 999 (1971).

SUMMARY OF THE INVENTION

The object of the present invention is to provide a commercially advantageous method of optical resolution of DL-cysteine using optically active mandelic acid, not taking the steps of substituting the amino group and the thiol group but directly from DL-form to the optically active forms of a high purity with a high yield.

The method of the present invention is characterized in that an optically active mandelic acid is reacted with DL-cysteine to form a complex, and that the complex substance is resolved by utilizing difference in solubilities thereof.

PREFERRED EMBODIMENTS OF THE INVENTION

The first step of carrying out the present method is to dissolve free DL-cysteine or cysteine containing excess amount of one of the enantiomers thereof in a liquid medium. Also, optically active mandelic acid is dissolved in the same kind of liquid medium. The latter solution (mandelic acid solution) is gradually added to the former solution (cysteine solution). Then, the less soluble complex will preferentially precipitates or crystallizes out in the mixed solution. Separation of the solid from the liquid gives L-cysteine L-mandelic acid or D-cysteine D-mandelic acid.

From these complexes substances, optically active cysteine can be obtained by decomposing the complex with a mineral acid, concentrating, and extracting the mandelic acid with an organic solvent, and optionally, recrystallization.

Preferable materials for the liquid medium are, usually, water, methanol, ethanol, 1-propanol, 2-propanol, and mixtures thereof.

At the crystallization, seeding is not always necessary but, in order to facilitate the crystallization, it is useful to add a small amount of the less soluble complex to the solution.

There is no particular limit in the addition ratio of cysteine and mandelic acid. It is the most preferable to use mandelic acid in the amount equivalent to the content of the optically active cysteine from the view point of the resolution efficiency.

The starting cysteine may be not only the above mentioned free cysteine, but also of the other forms such as hydrochloride and sulfate. In the latter case, the resolution can be facilitated by adding a substance, e.g., sodium hydroxide, which release cysteine at the time of the reaction. Even if the hydrochloride, sulfate or the like of cysteine remaines in the reaction solution, there will be no trouble in the resolution.

The reaction temperature and pressure may be chosen from wide ranges. However, it is preferable that, in view of the relatively low stability of cysteine, the reaction is carried out at a room temperature or, even under cooling with cold water or ice water.

The present invention will now be illustrated with Examples below:

EXAMPLE I 17.6 g (0.10 mole) of DL-cysteine hydrochloride was dissolved in 10 ml of water. Also, 3.2 g (0.08 mole) of sodium hydroxide was dissolved in 20 ml of water, and, in the resulting solution, 7.6 g (0.05 mole) of L-(+)-mandelic acid was dissolved. These two solutions were mixed, and 5 mg of crystal of less soluble L-cysteine.L-mandelic acid was seeded to the mixed solution, which was allowed to stand at a room temperature for 1.5 hours. Precipitated crystal was separated by filtration, washed with 3.0 ml of water, and then dried to give 10.01 g of crystal of L-cysteine.L-mandelic acid. $[\alpha]_{435}^{20} + 195.0°$ (C=1.00, N-HCl). Through recrystallization of 9.91 g of the crude crystal with 15 ml of water, 6.81 g of refined crystal was obtained. $[\alpha]_{435}^{21.5} + 202.3°$ (C=1.00, 2N-HCl).

18.6 ml of 2N-HCl was added to 6.76 g of the refined crystal to completely dissolve the crystal by heating to 40° to 50° C., and then, the solution was cooled to 15° C. for 30 minutes. Precipitated crystal was filtered out, and the filtrate solution was evaporated to dry. 20 ml of isopropyl ether was added to the residue, and the admixture was stirred for 30 minutes. Isopropyl ether phase was separated by decantation, and further 10 ml of isopropyl ether was added for washing. Through recrystallization of the residual solid from 5 ml of 95 % ethanol, 3.31 g of L-cysteine hydrochloride was obtained. $[\alpha]_D^{21} + 5.6°$ (C=1.00, 2N-HCl) m.p. 179° to 181° C. (dec.).

EXAMPLE II 35.2 g (0.20 mole) of DL-cysteine hydrochloride was dissolved in 20 ml of water. Also, 6.4 g (0.16 mole) of sodium hydroxide was dissolved in 40 ml of water, and, in the resulting solution 15.2 g (0.10 mole) of D-(-)-mandelic acid was dissolved. These two solutions were mixed, and allowed to stand at a room temperature for 3.5 hours. Precipitated crystal was taken out by filtration, washed with 6.0 ml of water, and then dried to give 19.78 g of D-cysteine.D-mandelic acid. $[\alpha]_{435}^{21} -197.2°$ (C =1.00, 2N-HCl) Through recrystallization of 19.73 g of the crude crystal with 30 ml of water, 13.86 g of refined crystal was obtained. $[\alpha]_{435}^{18} -203.2°$ (C=1.00, 2N-HCl).

19.8 ml of 2.5 N-HCl was added to 13.71 g of the refined crystal to completely dissolve the crystal by heating to 40° to 50° C., and then, the solution was cooled to 12° C. for 30 minutes. Precipitated crystal was filtered out, and the filtrate solution was evaporated to dry. 30 ml of isopropyl ether was added to the residue, and the admixture was heated to 40° to 50° C. and stirred for 30 minutes. Isopropyl ether phase was separated by decantation, and further, each 15 ml of isopropyl ether was used twice for the same procedure. Through recrystallization of the residual solid from 8 ml of 95% ethanol, 4.93 g of D-cysteine hydrochloride was obtained. $[\alpha]_D^{21} -5.7°$ (C=1.00, 2N-HCl) m.p. 179° to 181° C. (dec.).

EXAMPLE III 17.6 g (0.10 mole) of DL-cysteine hydrochloride was dissolved in 20 ml of water. Also, 2.8 g (0.07 mole) of sodium hydroxide was dissolved in 40 ml of water, and, in the resulting solution 9.12 g (0.06 mole) of L-(+)-mandelic acid was dissolved. These two solutions were mixed, and 5 mg of crystal of less soluble L-cysteine.L-mandelic acid was seeded to the mixed solution, which was allowed to stand at a room temperature for 1.5 hours, and then cooled with ice water for 1.5 hours. Precipitated solution was separated by filtration, washed with 6.0 ml of water, and then dried to give 6.69 g of crude crystal of L-cysteine.L-mandelic acid. $[\alpha]_{435}^{20} +202.0°$ (C=1.00, 2N-HCl).

2.73 g of the crude crystal was dissolved in 20 ml of 0.5 N-NaOH, and, after addition of 0.16 g of ferric chloride to the resulting solution, pH of the solution was adjusted to 7 to 8 with 1N-NaOH. Air was blown into thus prepared solution for 1.5 hours, and formed crystal was filtered out. Washing of the crystal with 5 ml of water and drying gave 0.58 g of L-cystine. $[\alpha]_D^{23} -135.9°$ (C=1.00, 1N-HCl). Through recrystallization of 0.53 g of the crude crystal from 60 ml of water, 0.20 g of the refined crystal was obtained. $[\alpha]_D^{22} -212.7°$ (C=1.00, 1N-HCl).

EXAMPLE IV 175.6 g (1.00 mole) of DL-cysteine hydrochloride was dissolved in 100 ml of water. Also, 32.0 g (0.80 mole) of sodium hydroxide was dissolved in 170 ml of water, and, in the resulting solution 76.0 g (0.50 mole) of L-(+)-mandelic acid was dissolved. These two solutions were mixed, and 50 mg of crystal of less soluble L-cysteine L-mandelic acid was seeded to the mixed solution, which was cooled to 17° to 20° C. for 1.5 hours, and then, 7° to 10° C. for 2 hours. Precipitated crystal was separated by filtration, washed with 27 ml of water, and then dried to give 121.7 g of crystal of L-cysteine.L-mandelic acid. $[\alpha]_{435}^{22.5} +189.7°$ (C=1.00, 2N-HCl). Through recrystallization of the crude crystal with 150 ml of water, 91.5 g of refined crystal was obtained. $[\alpha]_{435}^{22.5} +202.0°$ (C=1.00, 2N-HCl).

86 ml of 3.8 N-HCl was added to 91.4 g of the refined crystal to completely dissolve the crystal by heating to about 60° C., and then, the solution was cooled to 7° to 10° C. for 30 minutes. Precipitated crystal was filtered out, and the filtrate solution was subjected to extraction with isopropyl ether in a liquid-liquid extractor for 2 hours. Water phase was concentrated to water content of 10%. 66 ml of isopropyl alcohol was added to the concentrated water solution for recrystallization, by which 33.8 g of L-cysteine hydrochloride was obtained. $[\alpha]_D^{25} +5.5°$ (C=1.00, 2N-HCl).

Then, 29.5 ml of concentrated hydrochloric acid was added to the mother liquor given by separation of the crude L-cysteine.L-mandelic acid, and the liquor was concentrated to the volume of about 200 ml. Precipitated sodium chloride was filtered out, and the filtrate solution was extracted with isopropyl ether in the liquid-liquid extractor for 2 hours. Water phase was concentrated to the volume of about 100 ml, and the concentrated solution received 98 ml of 20% sodium hydroxide aqueous solution for adjusting pH of the solution to 5 to 6. Water was so added to the solution that the volume increased to 300 ml, and 68.4 g (0.45 mole) of D-(-)-mandelic acid was added to the diluted solution, which was heated to about 70° C. for dissolution. 50 mg of less soluble D-cysteine.D-mandelic acid was seeded to the solution, and the solution was cooled to 17° to 20° C. for 1.5 hours, and then, 7 to 10° C. for 2 hours. Precipitated crystal was filtered out, washed with 25 ml of water, and then dried to give 124.3 g of crude crystal of D-cysteine.D-mandelic acid. $[\alpha]_{435}^{23.5} -162.9°$ (C=1.00, 2N-HCl).

Through adding 100 ml of water to the crude crystal, heating to 70° C., subsequent cooling and filtration, 80.5 g of refined crystal of D-cysteine.D-mandelic acid was obtained. $[\alpha]_{435} -198.9°$ (C=1.00, 2N-HCl).

The same procedures as described in connection with L-cysteine.L-mandelic acid were carried out using the refined crystal, and 36.0 g of D-cysteine hydrochloride was obtained. $[\alpha]_D^{21.5} -5.3°$ (C=1.00, 2N-HCl).

We claim:

1. A method of optical resolution of DL-cysteine comprising reacting an optically active mandelic acid with DL-cysteine to form a complex of two diastereomers, resolving the complex by fractional crystallization utilizing the differences in solubilities of the two diastereomers, decomposing either of the two diastereomers by a strong acid to salts of the optically active cysteine and the optically active mandelic acid, removing the optically active mandelic acid, and recovering the optically active cysteine.

* * * * *